US008207139B2

(12) United States Patent
Yang (10) Patent No.: US 8,207,139 B2
(45) Date of Patent: Jun. 26, 2012

(54) FUNCTION OF GPR4 IN VASCULAR INFLAMMATORY RESPONSE TO ACIDOSIS AND RELATED METHODS

(75) Inventor: Li Yang, Greenville, NC (US)

(73) Assignee: Li Yang, Greenville, NC (US)

( * ) Notice: Subject to any disclaimer, the term of this patent is extended or adjusted under 35 U.S.C. 154(b) by 0 days.

(21) Appl. No.: 12/882,187

(22) Filed: Sep. 14, 2010

(65) Prior Publication Data

US 2011/0081337 A1    Apr. 7, 2011

Related U.S. Application Data

(60) Provisional application No. 61/276,673, filed on Sep. 15, 2009.

(51) Int. Cl.
    *A61K 48/00*    (2006.01)
(52) U.S. Cl. ...... 514/44; 536/24.5; 536/24.31; 536/24.1
(58) Field of Classification Search ........................ None
    See application file for complete search history.

(56) References Cited

U.S. PATENT DOCUMENTS

2006/0067931 A1 *  3/2006  Lum ........................ 424/133.1
2006/0252679 A1 * 11/2006  Saki et al. ..................... 514/12

OTHER PUBLICATIONS

Jacoby E, Bouhelal R, Gerspacher M, Seuwen K (2006) The 7 TM G-protein-coupled receptor target family. ChemMedChem 1: 761-782.
Ludwig MG, Vanek M, Guerini D, Gasser JA, Jones CE, et al. (2003) Proton-sensing G-protein-coupled receptors. Nature 425: 93-98.
Yang LV, Radu CG, Roy M, Lee S, McLaughlin J, et al. (2007) Vascular abnormalities in mice deficient for the G protein-coupled receptor GPR4 that functions as a pH sensor. Mol Cell Biol 27: 1334-1347.
Liu JP, Nakakura T, Tomura H, Tobo M, Mogi C, et al. (2010) Each one of certain histidine residues in G-protein-coupled receptor GPR4 is critical for extracellular proton-induced stimulation of multiple G-protein-signaling pathways. Pharmacol Res 61: 499-505.
Zhu K, Baudhuin LM, et al. (2001) Sphingosylphosphorylcholine and lysophosphatidylcholine are ligands for the G protein-coupled receptor GPR4. J Biol Chem 276: 41325-41335. Retraction, 2005, vol. 280, 43280.
Kim KS, Ren J, Jiang Y, Ebrahem Q, Tipps R, et al. (2005) GPR4 plays a critical role in endothelial cell function and mediates the effects of sphingosylphosphorylcholine. Faseb J 19: 819-821.
Qiao J, Huang F, Naikawadi RP, Kim KS, Said T, et al. (2006) Lysophosphatidylcholine Impairs Endothelial Barrier Function through the G Protein-Coupled Receptor, GPR4. Am J Physiol Lung Cell Mol Physiol 291: L91-101.
Zou Y, Kim CH, Chung JH, Kim JY, Chung SW, et al. (2007) Upregulation of endothelial adhesion molecules by lysophosphatidylcholine. Involvement of G protein-coupled receptor GPR4. FEBS J 274: 2573-2584.
Nedergaard M, Kraig RP, Tanabe J, Pulsinelli WA (1991) Dynamics of interstitial and intracellular pH in evolving brain infarct. Am J Physiol 260: R581-588.
Hunt JF, Fang K, Malik R, Snyder A, Malhotra N, et al. (2000) Endogenous airway acidification. Implications for asthma pathophysiology. Am J Respir Crit Care Med 161: 694-699.
Lardner A (2001) The effects of extracellular pH on immune function. J Leukoc Biol 69: 522-530.
Stefanelli T, Malesci A, De La Rue SA, Danese S (2008) Anti-adhesion molecule therapies in inflammatory bowel disease: touch and go. Autoimmun Rev 7: 364-369.
Sughrue ME, Mehra A, Connolly ES, Jr., D'Ambrosio AL (2004) Anti-adhesion molecule strategies as potential neuroprotective agents in cerebral ischemia: a critical review of the literature. Inflamm Res 53: 497-508.
Amantea D, Nappi G, Bernardi G, Bagetta G, Corasaniti MT (2009) Post-ischemic brain damage: pathophysiology and role of inflammatory mediators. FEBS J 276: 13-26.
Poschet J, Perkett E, Deretic V (2002) Hyperacidification in cystic fibrosis: links with lung disease and new prospects for treatment. Trends Mol Med 8: 512-519.
Gatenby RA, Gillies RJ (2004) Why do cancers have high aerobic glycolysis? Nat Rev Cancer 4: 891-899.
Fire A, Xu S, Montgomery MK, Kostas SA, Driver SE, et al. (1998) Potent and specific genetic interference by double-stranded RNA in *Caenorhabditis elegans*. Nature 391: 806-811.
Reese, C. B. (2002) The chemical synthesis of oligo- and poly-nucleotides: a personal commentary. Tetrahedron 58: 8893-8920.
Castanotto D, Rossi JJ (2009) The promises and pitfalls of RNA-interference-based therapeutics. Nature 457: 426-433.
Biroccio A, Leonetti C, Zupi G (2003) The future of antisense therapy: combination with anticancer treatments. Oncogene 22: 6579-6588.
Williams C (2004) cAMP detection methods in HTS: selecting the best from the rest. Nat Rev Drug Discov 3: 125-135.
Kabir S (2002) Immunoglobulin purification by affinity chromatography using protein A mimetic ligands prepared by combinatorial chemical synthesis. Immunol Invest 31: 263-278.
Kohler G, Milstein C (1975) Continuous cultures of fused cells secreting antibody of predefined specificity. Nature 256: 495-497.
Weiner LM (2006) Fully human therapeutic monoclonal antibodies. J Immunother 29: 1-9.
Green LL, Hardy MC, Maynard-Currie CE, Tsuda H, Louie DM, et al. (1994) Antigen-specific human monoclonal antibodies from mice engineered with human lg heavy and light chain YACs. Nat Genet 7: 13-21.
Fishwild DM, O'Donnell SL, Bengoechea T, Hudson DV, Harding F, et al. (1996) High-avidity human IgG kappa monoclonal antibodies from a novel strain of minilocus transaenic mice. Nat Biotechnol 14: 845-851.

(Continued)

*Primary Examiner* — Kimberly Chong (57) ABSTRACT

The present invention relates to methods for the treatment of inflammation. Specifically, disclosed herein are methods to inhibit vascular inflammatory responses by inhibiting the proton-sensing GPR4 receptor. Such methods can be utilized, most preferably, in pharmaceutical compositions to modulate inflammation in acidosis-related diseases.

1 Claim, 9 Drawing Sheets

OTHER PUBLICATIONS

Mendez MJ, Green LL, Corvalan JR, Jia XC, Maynard-Currie CE, et al. (1997) Functional transplant of megabase human immunoglobulin loci recapitulates human antibody response in mice. Nat Genet 15: 146-156.

McCafferty J, Griffiths AD, Winter G, Chiswell DJ (1990) Phage antibodies: filamentous phage displaying antibody variable domains. Nature 348: 552-554.

Marks JD, Hoogenboom HR, Bonnert TP, McCafferty J, Griffiths AD, et al. (1991) By-passing immunization. Human antibodies from V-gene libraries displayed on phage. J Mol Biol 222: 581-597.

Kiely JM, Luscinskas FW, Gimbrone MA, Jr. (1999) Leukocyte-endothelial monolayer adhesion assay (static conditions). Methods Mol Biol 96: 131-136.

Madonna R, et al (2004) Insulin enhances vascular cell adhesion molecule-1 expression in human cultured endothelial cells through a pro-atherogenic pathway mediated by p38 mitogen-activated protein-kinase. Diabetologia 47: 532-536.

Hochbaum D, Hong K, Barila G, Ribeiro-Neto F, Altschuler DL (2008) Epac, in synergy with cAMP-dependent protein kinase (PKA), is required for cAMP-mediated mitogenesis. J Biol Chem 283: 4464-4468.

* cited by examiner

Figure 1

| GeneID | Gene Symbol | Gene Name | Fold |
|---|---|---|---|
| 3576 | IL8 | Interleukin 8 | 18.0 |
| 2920 | CXCL2 | Chemokine (C-X-C motif) ligand 2 | 9.7 |
| 2921 | CXCL3 | Chemokine (C-X-C motif) ligand 3 | 9.0 |
| 6372 | CXCL6 | Chemokine (C-X-C motif) ligand 6 | 8.0 |
| 1437 | CSF2 | Colony stimulating factor 2 | 7.4 |
| 6364 | CCL20 | Chemokine (C-C motif) ligand 20 | 6.1 |
| 6354 | CCL7 | Chemokine (C-C motif) ligand 7 | 5.8 |
| 6376 | CX3CL1 | Chemokine (C-X3-C motif) ligand 1 | 5.2 |
| 2919 | CXCL1 | Chemokine (C-X-C motif) ligand 1 | 4.1 |
| 7412 | VCAM1 | Vascular cell adhesion molecule 1 | 8.2 |
| 6401 | SELE | Selectin E | 4.4 |

Figure 2

| GeneID | Gene Symbol | Gene Name | Fold |
|---|---|---|---|
| 3576 | IL8 | Interleukin 8 | 56.8 |
| 2920 | CXCL2 | Chemokine (C-X-C motif) ligand 2 | 48.9 |
| 2921 | CXCL3 | Chemokine (C-X-C motif) ligand 3 | 27.3 |
| 6372 | CXCL6 | Chemokine (C-X-C motif) ligand 6 | 7.7 |
| 1437 | CSF2 | Colony stimulating factor 2 | 6.2 |
| 6364 | CCL20 | Chemokine (C-C motif) ligand 20 | 72.4 |
| 6354 | CCL7 | Chemokine (C-C motif) ligand 7 | 5.4 |
| 6376 | CX3CL1 | Chemokine (C-X3-C motif) ligand 1 | 13.4 |
| 2919 | CXCL1 | Chemokine (C-X-C motif) ligand 1 | 18.6 |
| 3552 | IL1A | Interleukin 1, alpha | 19.8 |
| 5743 | PTGS2 | Prostaglandin-endoperoxide synthase 2 | 17.3 |
| 374 | AREG | Amphiregulin | 12.8 |
| 4254 | KITLG | KIT ligand | 6.8 |
| 6347 | CCL2 | Chemokine (C-C motif) ligand 2 | 6.5 |
| 51561 | IL23A | Interleukin 23, alpha subunit | 5.4 |
| 970 | TNFSF7 | Tumor necrosis factor (ligand) superfamily member 7 | 4.0 |
| 7185 | TRAF1 | Tumor necrosis factor receptor-associated factor 1 | 9.3 |
| 3604 | TNFRSF9 | Tumor necrosis factor receptor superfamily member 9 | 5.1 |
| 7127 | TNFAIP2 | Tumor necrosis factor, alpha-induced protein 2 | 5.9 |
| 5971 | RELB | V-rel reticuloendotheliosis viral oncogene homolog B | 8.2 |
| 64332 | NFKBIZ | Nuclear factor of kappa light polypeptide gene enhancer in B-cells inhibitor, zeta | 12.8 |
| 4792 | NFKBIA | Nuclear factor of kappa light polypeptide gene enhancer in B-cells inhibitor, alpha | 8.8 |
| 7412 | VCAM1 | Vascular cell adhesion molecule 1 | 73.3 |
| 6401 | SELE | Selectin E | 305.9 |
| 9076 | CLDN1 | Claudin 1 | 10.6 |
| 969 | CD69 | CD69 antigen | 74.5 |

| siRNA #1 | Sense: 5'- AUCCCUCUACAUCUUUGUCAU -3' (SEQ ID NO:1)<br>Antisense: 5'- AUGACAAAGAUGUAGAGGGAU -3' (SEQ ID NO:2) |
|---|---|
| siRNA #2 | Sense: 5'- CAAGAGGAACAGCACAGCCAA -3' (SEQ ID NO:3)<br>Antisense: 5'- UUGGCUGUGCUGUUCCUCUUG -3' (SEQ ID NO:4) |

SEQUENCE LISTING

<160> NUMBER OF SEQ ID NOS: 4

<210> SEQ ID NO 1
<211> LENGTH: 21
<212> TYPE: RNA
<213> ORGANISM: Homo sapiens

<400> SEQUENCE: 1

```
aucccucuac aucuuuguca u                                  21

<210> SEQ ID NO 2
<211> LENGTH: 21
<212> TYPE: RNA
<213> ORGANISM: Homo sapiens

<400> SEQUENCE: 2
augacaaaga uguagaggga u                                  21

<210> SEQ ID NO 3
<211> LENGTH: 21
<212> TYPE: RNA
<213> ORGANISM: Homo sapiens

<400> SEQUENCE: 3
caagaggaac agcacagcca a                                  21

<210> SEQ ID NO 4
<211> LENGTH: 21
<212> TYPE: RNA
<213> ORGANISM: Homo sapiens

<400> SEQUENCE: 4
uuggcugugc uguuccucuu g                                  21
```

FUNCTION OF GPR4 IN VASCULAR INFLAMMATORY RESPONSE TO ACIDOSIS AND RELATED METHODS

RELATED APPLICATION

This application claims benefits of U.S. Provisional Application Ser. No. 61/276,673, filed Sep. 15, 2009.

FIELD OF THE INVENTION

The present invention relates to the field of the treatment of inflammation. Methods are provided to inhibit the GPR4 receptor for inhibiting inflammatory responses.

BACKGROUND OF THE INVENTION

G protein-coupled receptors (GPCRs) are the largest family of cell surface receptors that are involved in many aspects of pathophysiological processes. There are approximately 800 GPCRs in the human genome, and about 30 GPCRs have been validated as therapeutic targets that account for more than 30 percent of marketed drugs for a variety of diseases (Jacoby E. et al. 2006, *ChemMedChem* Vol. 1, pp. 761-782). However, hundreds of GPCRs remain to be characterized and explored as potential pharmaceutical targets. There is a significant interest in defining the function of the GPCRs in physiology and pathological conditions and then modulating the GPCR signaling pathways for the treatment of diseases. Drug discovery efforts have been concentrated on identifying compounds that either stimulate or inhibit GPCR activities.

GPR4 (Gene ID: 2828), a member of the proton-sensing GPCR family, has recently been identified as a novel pH sensor (Ludwig M. G. et al. 2003, *Nature* Vol. 425, pp. 93-98; Yang L. V. et al. 2007, *Mol. Cell. Biol.* Vol. 27, pp. 1334-1347; Liu J. P. et al. 2010, *Pharmacol Res.* Vol. 61, pp. 499-505). GPR4 encodes a cell surface receptor consisting of 362 amino acids and is expressed in a wide range of tissues such as the lung, kidney, heart, intestine, and liver. GPR4 is highly conserved during evolution, with more than 90% protein sequence homology among mammalian orthologs and more than 70% homology between human and zebrafish orthologs. However, the biological function of GPR4 is not clearly defined. GPR4 was previously reported to be a receptor for the lysolipids sphingosylphosphorylcholine (SPC) and lysophosphatidylcholine (LPC), but this observation has not been confirmed and the original publication has been retracted (Zhu K. et al. 2001, *J Biol Chem* Vol. 276, 41325-41335. Retraction, 2005, Vol. 280, 43280). Several studies indicated that GPR4 mediates the SPC-induced endothelial tube formation, LPC-induced impairment of endothelial barrier function, and LPC-induced VCAM-1 expression (Kim K. S. et al. 2005, *Faseb J.* Vol. 19, pp. 819-821; Qiao J. et al. 2006, *Am J Physiol Lung Cell Mol Physiol.* Vol. 291, pp. L91-101; Zou Y. et al. 2007, *FEBS J.* Vol. 274, pp. 2573-2584). However, as the ligand-receptor relationship between SPC, LPC and GPR4 is not validated, it is unclear whether GPR4 directly or indirectly mediates the biological effects of the lysolipids SPC and LPC.

More recent studies demonstrate that GPR4 predominantly functions as a proton sensor activated by extracellular acidic pH (Ludwig M. G. et al. 2003, *Nature* Vol. 425, pp. 93-98; Yang L. V. et al. 2007, *Mol. Cell. Biol.* Vol. 27, pp. 1334-1347; Liu J. P. et al. 2010, *Pharmacol Res.* Vol. 61, pp. 499-505). Several extracellular histidine residues of GPR4 are important for the proton sensing and the receptor activation. Acidosis-induced GPR4 activation stimulates the Gs/cAMP signaling in endothelial cells and regulates the growth of microvessels (angiogenesis) (Yang L. V. et al. 2007, *Mol. Cell. Biol.* Vol. 27, pp. 1334-1347). Since blood vessels form and/or function in acidic tissue microenvironments in many pathological conditions such as inflammation, ischemia and cancer, it is very important to delineate how acidosis regulates the growth and function of blood vessels, by which new therapeutic opportunities may be provided. It should be pointed out that the growth of new blood vessels (i.e. angiogenesis) and the function of blood vessels (e.g. vascular adhesion and vessel tone) are distinct aspects of vascular biology and involved in different diseases.

Local or systemic acidosis is associated with a variety of pathological conditions such as inflammation, ischemia, tumor, diabetic ketoacidosis, and lung and renal diseases due to defective blood flow, hypoxia, and glycolytic metabolism (Nedergaard M. et al. 1991, *Am J Physiol.* Vol. 260, R581-588; Hunt J. F. et al. 2000, *Am J Respir Crit Care Med.* Vol. 161, pp. 694-699; Lardner, A. 2001, *J Leukoc Biol.* Vol. 69, pp. 522-530). For instance, interstitial pH in ischemic organs often decreases to 7.0-6.0 and sometimes below 6.0. Acidosis has profound effects on blood vessels, immune cells, inflammatory responses and tissue injury, but it is previously unknown whether GPR4 regulates vascular endothelium-leukocyte interaction and inflammation in response to acidosis.

The interaction between vascular endothelial cells and blood cells plays critical roles in inflammatory responses and thrombosis. Adhesion of leukocytes to endothelium is an important early step through which immune cells extravasate into inflammatory tissues to perform effector function. In the microenvironment, endothelial cells and blood cells are activated to trigger an inflammatory phenotype such as the increase of adhesion molecules and secretion of cytokines and chemokines. Inhibition of endothelium-blood cell interaction has been pursued as therapeutic approaches to treat inflammation (Stefanelli T. et al. 2008, *Autoimmun Rev.* Vol. 7, pp. 364-369). In the present invention, GPR4 is identified as a new therapeutic target for inhibiting acidosis-induced inflammatory responses of endothelial cells and the related methods for the inhibition are provided. It would be an advance in the art to provide method to treat inflammation in acidosis-related diseases.

SUMMARY OF THE INVENTION

The present invention provides methods and reagents for inhibiting inflammation. In particular, the invention provides the GPR4 receptor that is activated by acidosis to increase the expression of inflammatory cytokines, chemokines, enzymes, and adhesion molecules in vascular endothelial cells. The invention also provides small interfering RNA molecules that inhibit the expression of the GPR4 receptor and reduce inflammatory responses of endothelial cells. Accordingly, the present invention can be used to treat inflammation by inhibiting the expression and/or activity of the GPR4 receptor, and to identify inhibitors of the GPR4 receptor.

According to some embodiments of the invention, activation of GPR4 by acidosis increases the inflammatory responses of vascular endothelial cells, which includes the increased expression of inflammatory cytokines, chemokines, enzymes, and adhesion molecules as shown by microarray analysis and real-time RT-PCR. These results indicate that GPR4 is a new molecular target that regulates inflammatory responses.

In some embodiments, activation of GPR4 by acidosis increases the adhesion of human umbilical vein endothelial cells (HUVECs) with monocyte and neutrophil cells. Consistently, the inhibition of GPR4 expression by small interfering RNA (siRNA) molecules reduces acidosis-induced adhesiveness of endothelial cells. These results indicate a new approach to control endothelium-blood cell adhesion and inflammatory response by modulating GPR4.

In some embodiments, inhibition of cAMP production using the adenylate cyclase inhibitors, 2',5'-dideoxyadenosine or SQ 22536, abolishes acidosis/GPR4-induced endothelial cell adhesion. Furthermore, the effector of cAMP, Epac but not PKA, is important for the signaling transduction. These results indicate that acidosis/GPR4 signaling regulates vascular endothelial cell adhesion through the Gs/cAMP/Epac pathway.

The present invention, therefore, relates to using GPR4 inhibitors to treat inflammation. Such GPR4 inhibitors can include, but not limited to, small inhibiting RNA molecules, chemical inhibitors, and antibodies. The inflammatory conditions include arthritis, asthma, ischemia-reperfusion injury, heart attack, stroke, limb ischemia, kidney ischemia, atherosclerosis, psoriasis, cancer, sickle cell disease, chronic pulmonary obstructive diseases, metabolic acidosis, cystic fibrosis, and inflammatory bowel disease.

In particular embodiments, the human GPR4 inhibitor is short interfering RNA (siRNA) molecules. The siRNA molecules are double-stranded and have the following nucleotide sequences:

```
Sense:
5'-AUCCCUCUACAUCUUUGUCAU-3'   (SEQ ID NO: 1)
and

Antisense:
5'-AUGACAAAGAUGUAGAGGGAU-3'   (SEQ ID NO: 2)
Or

Sense:
5'-CAAGAGGAACAGCACAGCCAA-3'   (SEQ ID NO: 3)
and

Antisense:
5'-UUGGCUGUGCUGUUCCUCUUG-3'   (SEQ ID NO: 4)
```

The present invention also encompasses the use of the siRNA molecules in the treatment of inflammation in arthritis, asthma, ischemia-reperfusion injury, heart attack, stroke, limb ischemia, kidney ischemia, atherosclerosis, psoriasis, cancer, sickle cell disease, chronic pulmonary obstructive diseases, metabolic acidosis, cystic fibrosis, and inflammatory bowel disease.

The present invention also encompasses the use of the detection of GPR4 activation for diagnosing inflammation.

DETAILED DESCRIPTION

Unless specified otherwise, all terms used in the present invention have the same meaning as commonly understood by those skilled in the art.

"GPR4" comprises any one of the following: (1) the nucleotide sequence identified as GenBank accession no. NM_005282; or (2) the protein sequence identified as GenBank accession no. NP_005273; or (3) any homologs of the above described sequences.

The term "inflammation" means the complex biological response of an organism to exogenous or endogenous stimuli, which involves the blood vessel, immune system, and local tissue. Pathological changes during inflammation include the increase of blood vessel adhesion and permeability, accumulation of immune cells at inflammatory sites, production of inflammatory mediators, and healing and, sometimes, destruction of local tissues.

The term "acidosis" means the increase of tissue acidity locally or systemically in the body. The physiological pH of most tissues and arterial blood in human body is around pH 7.4. Decrease of pH below 7.35 is considered as acidosis. The severity of acidosis is correlated with the degree of pH drop.

The term "acidosis-related diseases" means the diseases in which acidosis exists either locally or systemically. These diseases include, but not limited to, arthritis, asthma, ischemia-reperfusion injury, heart attack, stroke, limb ischemia, kidney ischemia, atherosclerosis, psoriasis, cancer, sickle cell disease, chronic pulmonary obstructive diseases, metabolic acidosis, cystic fibrosis, and inflammatory bowel disease.

The term "compound" means a molecule that is a chemical, an oligo-nucleotide, a peptide, or an antibody.

The term "agonist" means a compound which binds and activates a receptor.

The term "antagonist" means a compound which binds but does not activate a receptor.

The term "inverse agonist" means a compound which binds, does not activate a receptor, but instead decreases the basal activity of a receptor.

The term "inhibit, inhibiting, or inhibition" means that a biological response is decreased in the presence of a compound when compared to in the absence of the compound.

The term "stimulate, stimulating, or stimulation" means that a biological response is increased in the presence of a compound when compared to in the absence of the compound.

The term "small interfering RNA" means a class of small RNA molecules which can be used to specifically inhibit the expression of a gene based on nucleotide sequence homology.

The order of the following sections is set forth for the clarity and efficiency of presentation and should not be construed as a limitation on the disclosure and the claims.

The present invention provides methods and reagents for the inhibition of inflammation in diseases. In particular, the invention provides the GPR4 receptor that is activated by acidosis to increase the expression of inflammatory cytokines, chemokines, enzymes, and adhesion molecules in vascular endothelial cells. The invention also provides small RNA molecules that inhibit the expression of GPR4 and reduce inflammatory responses of endothelial cells.

Accordingly, the present invention can be used to treat inflammation by inhibiting the expression and/or activity of GPR4, and also be used to identify inhibitors of GPR4. Such GPR4 inhibitors can include, but not limited to, small inhibiting RNA molecules, chemical inhibitors, and antibodies. The inflammatory conditions include arthritis, asthma, ischemia-reperfusion injury, heart attack, stroke, limb ischemia, kidney ischemia, atherosclerosis, psoriasis, cancer, sickle cell disease, chronic pulmonary obstructive diseases, inflammatory bowel disease, cystic fibrosis, and metabolic acidosis.

A. Introduction

Inflammation is a very common pathological condition that exists in a wide range of diseases, such as arthritis, asthma, ischemia-reperfusion injury, heart attack, stroke, limb ischemia, kidney ischemia, atherosclerosis, psoriasis, cancer, sickle cell disease, chronic pulmonary obstructive diseases, inflammatory bowel disease, and cystic fibrosis. On one side, inflammation is protective for the organism to eliminate exogenous or endogenous injurious stimuli. On the other side, uncontrolled and/or persisted inflammation causes tissue damages in the diseases such as these described above.

The vascular system and the immune system are critically involved in inflammation. In response to inflammatory stimuli, activated vascular endothelial cells that have increased expression of chemokines, cytokines, and adhesion molecules facilitate the recruitment of leukocytes to inflammatory sites. Leukocytes in the blood adhere to endothelial cells, transmigrate across the endothelium, enter inflamed tissues, release inflammatory mediators and cause the phenotype of inflammation. Blockade of vascular inflammatory molecules or inhibition of leukocytes has been used as effective strategies to treat inflammatory diseases (Sughrue M. E. et al. 2004, *Inflamm Res*. Vol. 53, pp. 497-508; Amantea D. et al. 2009, *FEBS J*. Vol. 276, pp. 13-26).

GPR4 is a proton-sensing G protein-coupled receptor (GPCR) which can be activated by extracellular protons (i.e. acidic pH). Local interstitial acidosis commonly exists in inflammatory tissues. For instance, acidic tissue pH is associated with asthma, arthritis, and cystic fibrosis (Hunt J. F. et al. 2000, *Am J Respir Crit Care Med*. Vol. 161, pp. 694-699; Lardner A. 2001, *J Leukoc Biol*. Vol. 69, pp. 522-530; Poschet J. et al. 2002, *Trends Mol Med*. Vol. 8, pp. 512-519). Acidosis is also frequently identified in ischemia and solid tumors in which inflammation plays an important role in disease progression (Gatenby R. A. and Gillies R. J. 2004, *Nat Rev Cancer* Vol. 4, pp. 891-899; Nedergaard M. et al. 1991, *Am J Physiol*. Vol. 260, pp. R581-588). Although prior art has described that activation of GPR4 by acidosis regulate the growth of blood vessels (i.e. angiogenesis) (Yang L. V. et al. 2007, *Mol. Cell. Biol*. Vol. 27, pp. 1334-1347), the effects of GPR4 activation by acidosis on blood vessel inflammation, a different aspect of vascular function from angiogenesis, are not known. GPR4 was previously reported to be a receptor for sphingosylphosphorylcholine (SPC) and lysophosphatidylcholine (LPC), but this observation has not been confirmed and the original publication has been retracted (Zhu K. et al. 2001, *J Biol Chem* Vol. 276, 41325-41335. Retraction, Vol. 280, 43280, 2005). Therefore, it is not obvious whether the function of GPR4 attributed to SPC and LPC is applicable to acidosis. Also, the response of GPR4 to SPC and LPC is a different aspect of biology from its response to acidosis. The present invention provides a novel function of GPR4 that activation of GPR4 by acidosis increases the expression of inflammatory chemokines, cytokines, and adhesion molecules in endothelial cells and augments the adhesiveness of endothelial cells with leukocytes. The present invention also provides methods to inhibit GPR4 for the treatment of inflammation in acidosis-related diseases.

B. Methods To Modulate Receptor Activity

B1. Small RNA inhibitors

RNA interference can be used to inhibit gene expression in cells and in whole organisms.

RNA interference is initiated by double-stranded RNA molecules and specifically inhibits gene expression based on nucleotide sequence homology between the double-stranded RNA and its target mRNA (Fire A. et al. 1998, *Nature* Vol. 391, pp. 806-811). In the present invention, the nucleotide sequence of human GPR4 (GenBank accession no. NM_005282) is used for the design of small interfering RNAs (siRNAs). Homologous genes of GPR4 in other species are also available at GenBank and can be used to design siRNAs for the inhibition of GPR4 expression in other species. In particular, RNA molecules consisting of 20-30 nucleotides will be designed to be homologous to the GPR4 mRNA sequence. The design of the oligo-nucleotides can be empirical or using computer-based programs publically available. Examples of human GPR4 small interfering RNAs are provided in FIG. 5. Both the sense strand and the complementary anti-sense strand will be synthesized using the standard oligonucleotide synthesis methods as available in the art (Reese C. B. 2002, *Tetrahedron*, Vol. 58, pp. 8893-8920). The sense and anti-sense strands will be annealed to form double-stranded oligo-nucleotides.

Several approaches can be used to deliver short interfering RNA (siRNA) molecules into cells for the silencing of gene expression (Castanotto D. and Rossi J.J. 2009, *Nature*, Vol. 457, pp. 426-433). One major strategy is to deliver chemically synthesized siRNAs into cells. Another major strategy is to use viral vectors to deliver short hairpin RNAs (shRNAs) that will generate siRNAs after transcription and processing in cells. In particular, chemically synthesized siRNAs can be encapsulated with polycation nanoparticles, or liposome for effective delivery into cells. This approach will result in a transient inhibition of gene expression typically in a range of a few days from a single dose of siRNAs. Delivery of multiple doses of siRNAs may be required to achieve a long-term inhibition of gene expression. Short hairpin RNAs (shRNAs) delivered by viral vectors can have stable gene silencing. shRNAs will be cloned into viral vectors and viral particles will be produced and used to transduce cells. After transcription in cells, shRNAs will be generated and processed into siRNAs to silence the target gene.

In addition to siRNAs, antisense RNA or DNA molecules can also be used to inhibit gene expression (Biroccio A. et al. 2003, *Oncogene* Vol. 22, pp. 6579-6588). A single-stranded antisense oligonucleotide complementary to GPR4 mRNA will be designed to inhibit GPR4 expression by hybridizing with GPR4 mRNA based on sequence homology. The location of the antisense oligonucleotide is preferred to be downstream and close to the translation start codon of GPR4 mRNA. Antisense RNA or DNA molecules inhibit gene expression mainly through preventing mRNA translation.

B2. Chemical Inhibitors

GPCRs are particularly amenable to small molecule modulation. Traditionally, GPCRs are important therapeutic targets of small molecule drugs that have been used in a wide range of diseases. Candidate compounds will be identified through high-throughput chemical screening. Activation of GPR4 in cells leads to the production of cyclic AMP (cAMP), a molecule that can be detected as a marker for the screening of GPR4 agonists, antagonists and inverse agonists. High-throughput assays based on cAMP measurement are commercially available (Williams C. 2004, *Nat Rev Drug Discov*. Vol. 3, pp. 125-135). As a general rule, homogeneous and non-radioactive assays are the preferred format, such as the HitHunter™ cAMP assay (DiscoveRx, Fremont, Calif.). To enable the high-throughput screening assay, NIH3T3 cell line, or other cell lines, will be genetically engineered to stably overexpress the human GPR4 receptor (designated as NIH3T3/GPR4 cells) using the retroviral transduction method (Yang L. V. et al. 2007, *Mol. Cell. Biol*. Vol. 27, pp. 1334-1347) or other transfection methods.

The cAMP-based high-throughput assay can be used to screen for both agonists and antagonists (or inverse agonists) of the GPR4 receptor. To screen for agonists, NIH3T3/GPR4 cells will be treated with compounds at a basic pH (such as pH 8.4) in which GPR4 has minimal basal activity, and compounds that stimulate GPR4 activity (as indicated by the increase of cAMP) will be identified as potential GPR4 agonists. To screen for antagonists (or inverse agonists), NIH3T3/GPR4 cells will be treated with compounds at a pH (such as pH 7.2) in which GPR4 is activated, and compounds that reduce GPR4 activity (as indicated by the decrease of cAMP) will be identified as potential GPR4 antagonists (or inverse agonists). Small molecule libraries, such as the Prestwick chemical library, Enzo Life Sciences chemical libraries, and other commercial compound libraries, will be screened to identify GPR4 agonists and antagonists (or inverse agonists). Candidate compounds will be counter screened against the parental NIH3T3 cells or NIH3T3 cells with other GPCR overexpression to identify GPR4-specific compounds.

GPR4 antagonists or inverse agonists will be used to inhibit the activity of GPR4 for the treatment of inflammation as described in the present invention.

B3. Antibodies

GPR4 specific antibodies may be used to inhibit the activity of GPR4. Methods are described herein for the production of antibodies. Such antibodies may include but not limited to polyclonal antibodies, monoclonal antibodies, and humanized monoclonal antibodies.

For the production of polyclonal antibodies (heterogeneous populations of antibody molecules), GPR4 proteins or protein fragments will be injected into host animals. Such host animals include but not limited to rabbit, goat, guinea pig, rat, and mouse. Adjuvants may be used to achieve maximal immune stimulation. Such adjuvants include Freund's adjuvant and the Ribi adjuvant system. After immunization, polyclonal antibodies will be purified from host animal sera using protein A/G or antigen-affinity chromatography (Kabir S. 2002, *Immunol Invest*. Vol. 31, pp. 263-78).

Monoclonal antibodies (homogeneous populations of antibody molecules) will be produced by the hybridoma technique (Kohler G. and Milstein C. 1975, *Nature* Vol. 256, pp. 495-497). The spleens cells isolated from mice that are immunized with GPR4 protein will be fused with human myeloma cells to form hybridoma cells. These hybridoma cells will be selected and enriched in the HAT medium that contains hypoxanthine, aminopterin, and thymidine. Monoclonal antibodies will be produced by the hybridoma cells in culture medium. The desired antibodies will be purified using protein A/G or antigen-affinity chromatography.

When monoclonal antibodies, derived from species such as mouse, are used as therapeutics in human patients, these antibodies may cause immune reaction and the production of human against mouse antibodies. To overcome this problem, methods have been developed to generate humanized monoclonal antibodies (Weiner L. M. 2006, *J Immunother.* Vol. 29, pp. 1-9). First, the production of human antibodies can be done in transgenic mice in which the mouse immunoglobulin genes have been disrupted and replaced with the human immunoglobulin genes (Green L. L. et al. 1994, *Nat Genet*. Vol. 7, pp. 13-21; Fishwild D. M. et al. 1996, *Nat Bioechnol*. Vol. 14, pp. 845-851; Mendez M. J. et al. 1997, *Nat Genet*. Vol 15, pp. 146-156). The transgenic mice will be immunized with GPR4 antigen and spleen cells from the mice will be isolated and used to make hybridoma cells as described above. Fully humanized antibodies will be produced from these hybridoma cells. Second, humanized antibodies can be generated using the phage display-based methods (McCafferty J. et al. 1990, *Nature*, Vol 348, pp. 552-554; Marks J. D. et al. 1991, *J Mol Biol*., Vol. 222, pp. 581-597). Phage libraries containing single-chain variable fragments (scFvs) of human antibodies will be screened against an antigen, said GPR4, and phages with high affinity with the antigen will be isolated. The scFv can be further optimized by mutagenesis, cloned into heavy and light chain expression vectors, and introduced into hybridoma cells for the production of humanized monoclonal antibodies.

The present invention provides the inhibition of the GPR4 receptor for the treatment of inflammation in a wide range of acidosis-related diseases. The methods to inhibit GPR4 include small RNA inhibitors, chemical inhibitors, and antibodies. The acidosis-related diseases include arthritis, asthma, ischemia-reperfusion injury, heart attack, stroke, limb ischemia, kidney ischemia, atherosclerosis, psoriasis, cancer, sickle cell disease, chronic pulmonary obstructive diseases, inflammatory bowel disease, cystic fibrosis, and metabolic acidosis.

EXAMPLES

The following examples are provided for the elucidation, but not limitation, of the present invention.

Example 1

Figure 4:
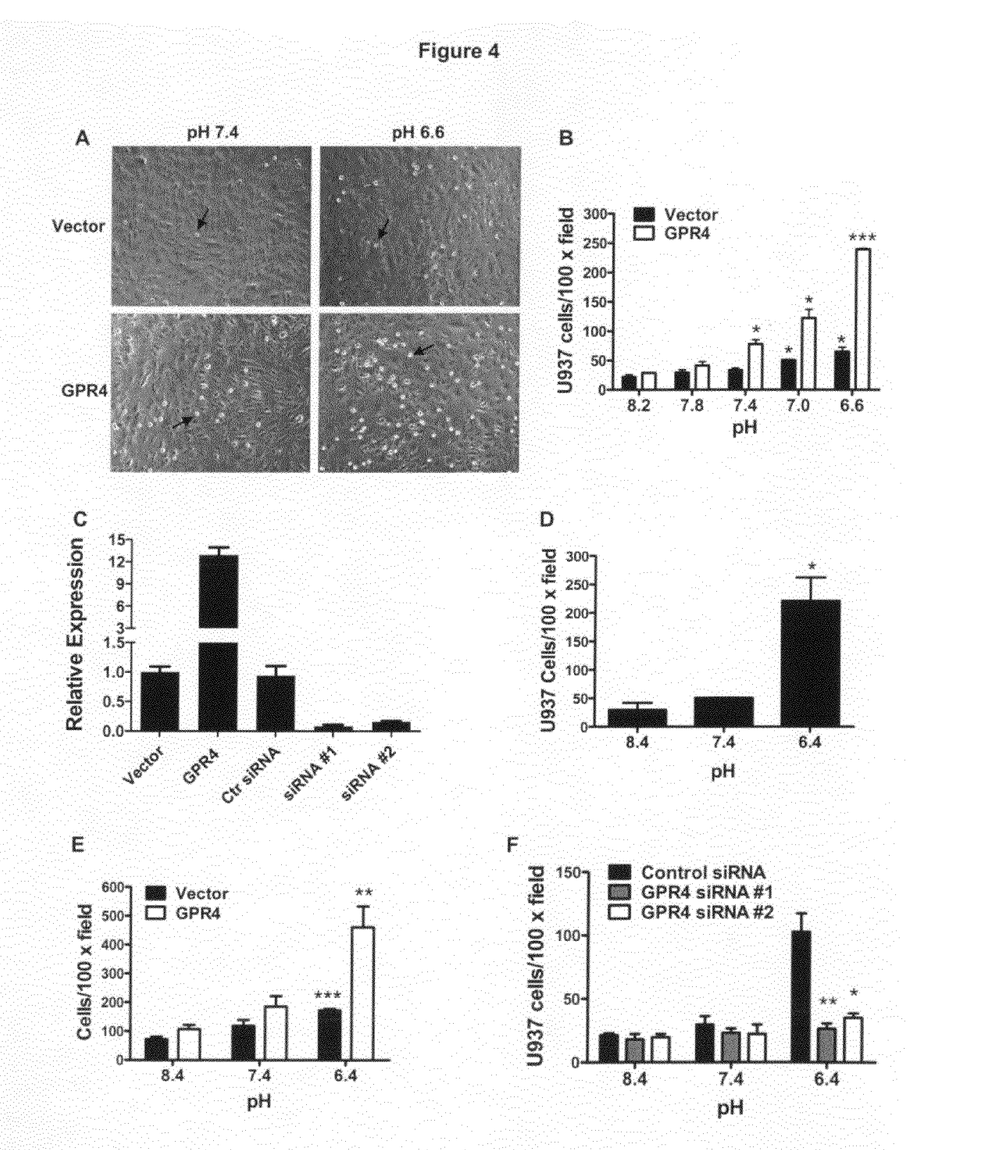
FIG. 4A is a micrograph of HUVEC endothelial cell adhesion when attached by U937 monocytic cells. HUVEC endothelial cells grow as a flat monolayer, and attached U937 cells are detected as small, round and reflectile cells under an inverted microscope with a 10×objective. Arrows indicate examples of attached U937 cells.
FIG. 4B sets forth data demonstrating that the activation of GPR4 by acidosis increases the adhesiveness of HUVEC endothelial cells by using the attachment of U937 monocytes as a functional readout. Results are depicted as the mean±SEM. *, P<0.05; ***, P<0.001; compared with the pH 8.2 group.
FIG. 4C sets forth data demonstrating the relative expression level of human GPR4 mRNAs measured by real-time RT-PCR in HUVEC endothelial cells with different genetic modifications such as the control vector, the GPR4-expression vector, the control siRNA, and the GPR4 siRNAs. Error bars are the mean±SEM.
FIG. 4D sets forth data demonstrating that acidosis increases the adhesiveness of HUVEC cells that stably overexpress the mouse GPR4-GFP fusion gene. Results are depicted as the mean±SEM. *, P<0.05.
FIG. 4E sets forth data demonstrating that activation of GPR4 by acidosis increases the adhesiveness of HUVEC cells with HL-60 promyelocytic cells (neutrophil-like cells). , P<0.01; *, P<0.001; compared with the pH 8.4 group. Error bars are the mean±SEM.
FIG. 4F sets forth data demonstrating that knockdown of GPR4 by small interfering RNA (siRNA) molecules reduces the adhesion of HUVEC cells. Results are depicted as the mean±SEM. *, P<0.05; **, P<0.01; compared with the control miRNA group at pH 6.4.

Activation of GPR4 by Acidosis Stimulates the Inflammatory Response of Vascular Endothelial Cells Cell cultures: Human umbilical vein endothelial cells (HUVECs) were cultured in the EGM-2 medium (Lonza, Walkersville, Md., USA). The pH of EGM-2 medium was buffered with 7.5 mM HEPES, 7.5 mM EPPS, and 7.5 mM MES (designated as EGM-2/HEM medium) and adjusted with sodium hydroxide or hydrochloric acid to desired pHs (Ludwig M. G. et al. 2003, *Nature* Vol. 425, pp. 93-98; Yang L. V. et al. 2007, *Mol. Cell. Biol*. Vol. 27, pp. 1334-1347). Human GPR4 cDNA was cloned into the retroviral expression system MSCV-IRES-GFP (Clontech, Mountain View, Calif., USA) and stably introduced into HUVEC endothelial cells through retroviral transduction (designated as HUVEC/GPR4 cells). HUVEC cells with the MSCV-IRES-GFP vector were also generated to be used as a control (designated as HUVEC/Vector cells). Compared to HUVEC/Vector cells that have endogenous GPR4 expression, GPR4 was overexpressed approximately 12 fold in HUVEC/GPR4 cells as measured by real-time RT-PCR (FIG. 4C).

Gene expression analysis: Microarray analysis was performed to determine the gene expression changes induced by acidosis/GPR4 signaling in HUVEC endothelial cells.

HUVEC/Vector and HUVEC/GPR4 cells were treated with EGM-2/HEM media at pH 6.4 (400 nM $H^+$) for 5 hours to activate the GPR4 receptor. As a control, the cells were treated with EGM-2/HEM media at pH 8.4 (4 nM $H^+$) for 5 hours, in which GPR4 only has basal level activity.

After the treatment, total RNA was extracted using the RNeasy Mini Plus Kit (QIAGEN, Valencia, CA, USA). For the microarray hybridization, total RNA from HUVEC cells treated with pH 6.4 (400 nM $H^+$) was labeled with Cy5 fluorescent dye to serve as the sample, whereas total RNA from HUVEC cells treated with pH 8.4 (4 nM $H^+$) was labeled with Cy3 fluorescent dye to serve as the control. The same amount of labeled sample and control RNAs was hybridized with the Agilent Whole Genome Microarray Chip (Agilent, Santa Clara, CA, USA). Hybridization signals were scanned and analyzed using the software available at the Genomics and Bioinformatics Core of the University of North Carolina at Chapel Hill.

Real-time reverse transcriptase-polymerase chain reaction (RT-PCR): Gene expression was assessed in HUVEC cells that were transduced with the control vector or GPR4 and treated with EGM-2/HEM media at pH 8.4, 7.4, or 6.4 for 5 h. Total RNA was extracted from HUVEC cells using the RNeasy Plus kit (QIAGEN, Valencia, CA, USA). 2.5 µg of total RNA was reverse transcribed using the SuperScript II reverse transcriptase (Invitrogen, CA, USA). Real-time PCR reagents were purchased from Applied Biosystems Inc (ABI, Foster City, CA, USA). Primers specific for the adhesion molecules were the TaqMan Gene Expression Assays from ABI: CXCL2, Hs00236966_ml; IL-8, Hs00174103_ml; VCAM-1, Hs01003372_ml; PTGS2, Hs00153133_ml.

Human glyceraldehydes-3-phophate dehydrogenase (GAPDH) TaqMan Gene Expression Assay (ABI, Cat. # 4333764T) was used as the internal control. Real-time PCR was performed in duplicate with a program of 50° C. for 2 min, 95° C. for 10 min followed by 40 cycles of 95° C. for 15 s and 60° C. for 1 min, and the data was acquired and analyzed using the ABI 7300-HT real-time PCR thermocycler.

Figure 1:
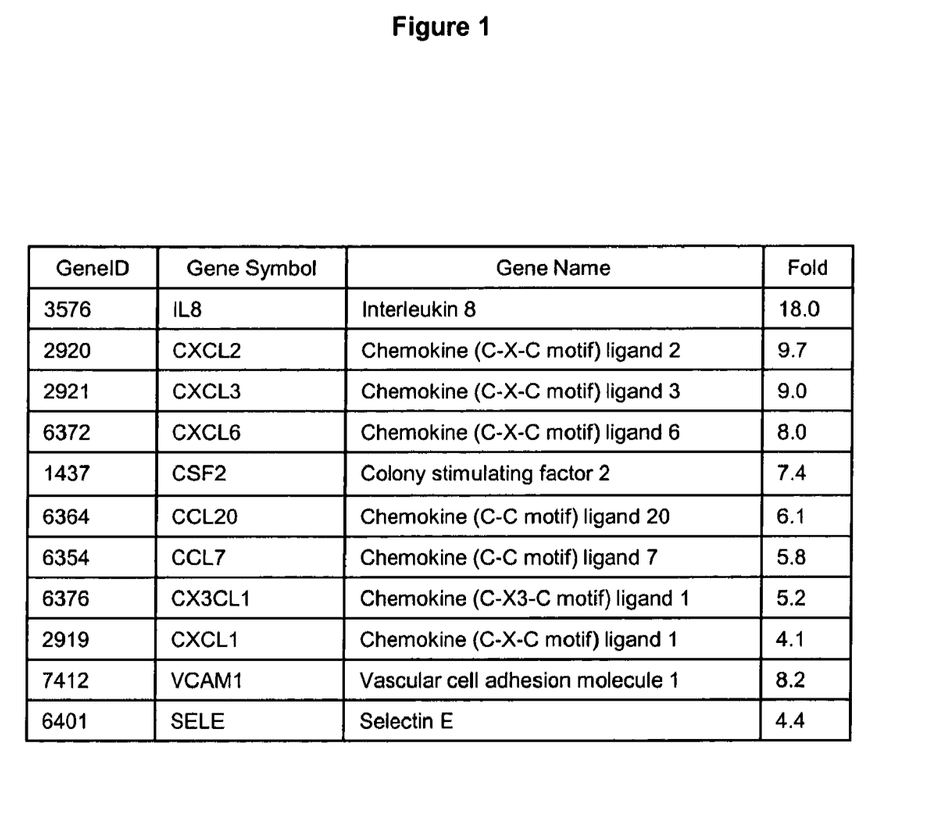
FIG. 1 is a table demonstrating that acidosis increases the expression of inflammatory cytokines, chemokines, and adhesion molecules in HUVEC endothelial cells transduced with the control vector (HUVEC/Vector cells) that have endogenous GPR4 gene expression. Fold of gene expression change: pH 6.4-treated HUVECNector cells are compared to pH 8.4-treated HUVECNector cells by microarray analysis.
Figure 2:
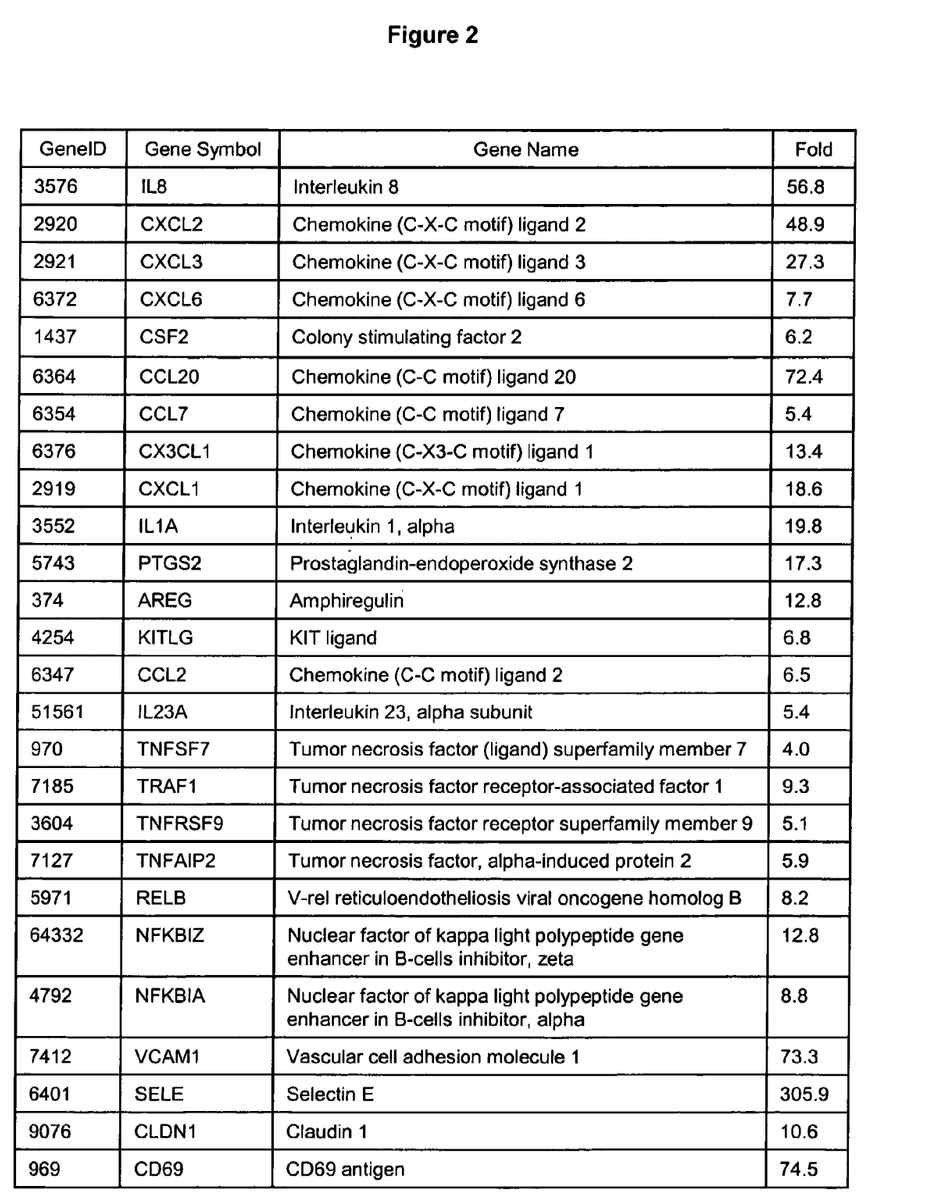
FIG. 2 is a table demonstrating that in GPR4-overexpressing HUVEC endothelial cells (HUVEC/GPR4 cells), the effects of GPR4 activation by acidosis are amplified and the expression of inflammatory cytokines, chemokines, and adhesion molecules is further increased. Fold of gene expression change: pH 6.4-treated HUVEC/GPR4 cells are compared to pH 8.4-treated HUVEC/GPR4 cells by microarray analysis.
Figure 3:
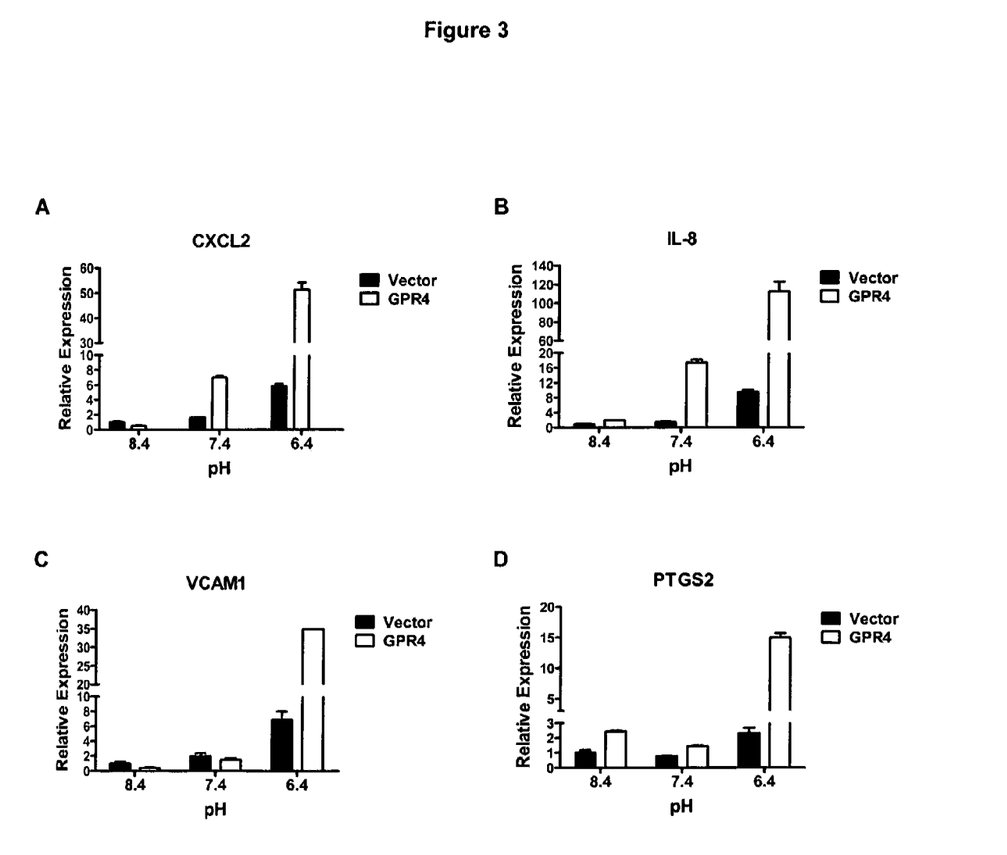
FIG. 3A sets forth data demonstrating that activation of GPR4 by acidosis increases the expression of CXCL2 mRNA in HUVEC cells as shown by real-time RT-PCR quantification. Values are normalized to the housekeeping gene GAPDH. The expression level of the target gene in HUVEC-Nector cells at pH 8.4 is set as 1. Error bars are the mean±SEM.
FIG. 3B sets forth data demonstrating that activation of GPR4 by acidosis increases the expression of IL-8 mRNA in HUVEC cells as shown by real-time RT-PCR quantification. Values are normalized to the housekeeping gene GAPDH. The expression level of the target gene in HUVECNector cells at pH 8.4 is set as 1. Error bars are the mean±SEM.
FIG. 3C sets forth data demonstrating that activation of GPR4 by acidosis increases the expression of VCAM-1 mRNA in HUVEC cells as shown by real-time RT-PCR quantification. Values are normalized to the housekeeping gene GAPDH. The expression level of the target gene in HUVEC-Nector cells at pH 8.4 is set as 1. Error bars are the mean±SEM.
FIG. 3D sets forth data demonstrating that activation of GPR4 by acidosis increases the expression of PTGS2 (COX-2) mRNA in HUVEC cells as shown by real-time RT-PCR quantification. Values are normalized to the housekeeping gene GAPDH. The expression level of the target gene in HUVECNector cells at pH 8.4 is set as 1. Error bars are the mean±SEM.

Results: The microarray results demonstrate that activation of GPR4 by acidosis in HUVEC endothelial cells stimulates the production of inflammatory chemokines, cytokines, and adhesion molecules, which play important roles in the recruitment, activation, and extravasation of immune cells. When the gene expression of HUVEC/Vector cells treated with different pHs (pH 6.4 versus 8.4) was compared, the incubation with acidic pH 6.4 for 5 hours induced the expression of a number of inflammatory genes by 4 to 18 fold (FIG. 1). These genes include inflammatory cytokines IL8 and CSF2, chemokines CXCL2, CXCL3, CXCL6, CCL20, CCL7, CX3CL1, and CXCL1, and adhesion molecules VCAM1 and selectin E. Importantly, overexpression of GPR4 in HUVEC/GPR4 cells further increased the changes of gene expression of several inflammatory genes, including IL8, CXCL2, CXCL3, CCL20, CX3CL1, CXCL1, VCAM1, SELE (FIG. 2), which indicate that the expression of these genes are induced by acidosis/GPR4 signaling. For some genes including CXCL6, CSF2, and CCL7, the fold of up-regulation responding to acidosis was similar in HUVECNector and HUVEC/GPR4 cells, which suggest that the induction of these genes is through GPR4-independent mechanisms. Furthermore, in addition to genes induced by acidosis in both HUVECNector and HUVEC/GPR4 cells, some genes show prominent up-regulation only in HUVEC/GPR4 cells. These genes include PTGS2 (COX-2), IL1A, amphiregulin, KIT ligand, CCL2, IL23A, claudin 1, CD69, and several genes involved in the TNF and NF kappa B pathways (FIG. 2). By real-time RT-PCR, the expression of 4 randomly selected acidosis/GPR4 target genes, including CXCL2, IL8, VCAM1, and PTGS2 (COX-2) have been confirmed (FIG. 3). Overall, the real-time RT-PCR results were highly consistent with the microarray results (FIGS. 1 and 2), showing that these inflammatory genes are induced by acidosis in HUVECNector cells and further increased in HUVEC/GPR4 cells.

Taken together, the results indicate that activation of GPR4 by acidosis stimulates the inflammatory response of endothelial cells, with up-regulation of inflammatory cytokines, chemokines, adhesion molecules, and other important inflammatory pathways including PTGS2 (COX2), TNF pathway, and NF kappa B pathway. These data demonstrate that the GPR4 receptor is a novel molecular target that is involved in inflammation in response to acidosis.

Example 2

Activation of GPR4 by Acidosis Increases Endothelial Cell Adhesion

Increase of cell adhesiveness is an important aspect of endothelial cell inflammatory response, and is critical for leukocytes to bind to blood vessel endothelium and extravasate into tissues to perform immunological function.

Cell adhesion assay: To examine the adhesion of HUVEC endothelial cells and to model the interaction between endothelium and immune cells, the HUVEC-U937 monocyte adhesion assay was used as a functional readout. The assay was performed as previously described with minor modifications (Kiely J. M., et al. 1999, *Methods Mol. Biol.* Vol. 96, pp. 131-136; Madonna R. et al. 2004, *Diabetologia* Vol. 47, pp. 532-536). In brief, HUVEC endothelial cells were cultured in a 24-well plate to form a confluent monolayer, and treated with EGM-2/HEM media at various pHs for 5 to 15 hours. After the pH treatment, HUVEC cells were washed once with DMEM medium (pH 7.4), and then U937 monocytic cells resuspended in DMEM with 10% fetal bovine serum (FBS) were added to the HUVEC monolayer to allow adhesion for 1 hour at pH 7.4. Non-adherent cells were removed by gently washing several times with DMEM medium. The attachment of U937 monocytic cells to the flat monolayer of HUVEC cells could be readily detected under an inverted microscope with a 10×objective (FIG. 4A).

Results: HUVECNector cells were treated with HEM-buffered EGM-2 media (EGM-2/HEM) at pH 8.2, 7.8 and 7.4 (6.3 nM, 15.8 nM, and 40 nM $H^+$, respectively), and the cells exhibited a low capacity to adhere U937 monocytes. The treatment of pH 7.0 and 6.6 (100 nM and 251 nM $H^+$, respectively) increased HUVECNector cell adhesion by 2- to 3-fold when compared to that at pH 8.2 (FIG. 4B). With the overexpression of human GPR4 in HUVEC/GPR4 cells, acidosis significantly increased the adhesiveness of HUVEC cells by 5- to 10-fold (FIG. 4B). As measured by real-time RT-PCR, GPR4 was over-expressed approximately 12-fold in HUVEC/GPR4 cells when compared to HUVECNector cells (FIG. 4C). Similarly, a significant increase of HUVEC adhesiveness upon acidic pH treatment was also observed in HUVEC cells overexpressing the mouse GPR4-GFP fusion gene (FIG. 4D). In addition to U937 monocytes, the adhesion of HUVEC cells with another type of leukocytes, the HL-60 promyelocytic cells (neutrophil-like cells), was also increased when HUVECNector and HUVEC/GPR4 cells were stimulated by acidosis (FIG. 4E). These results show that activation of GPR4 by acidosis induces an adhesive phenotype of HUVEC endothelial cells, which is important for the attachment of leukocytes and inflammatory responses.

Example 3

Inhibition of GPR4 Reduces Acidosis-Induced Endothelial Cell Adhesion

Figure 5:
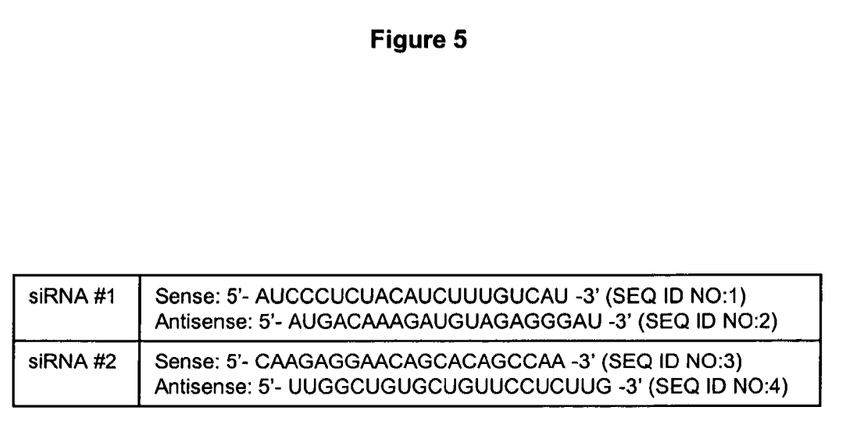
FIG. 5 is a table describing the nucleotide sequences of two small interfering RNA (siRNA) molecules of human GPR4.

Inhibition of GPR4 expression using siRNAs: To examine the effects of GPR4 inactivation on endothelial cell adhesion induced by acidosis, short interfering RNA (siRNA) molecules were used to knockdown the endogenous GPR4 gene expression in HUVEC cells. Two sets of siRNAs against human GPR4 have been designed (FIG. 5). The nucleotide sequences of the DNA template of the siRNA molecules are the following:

```
Sense:
5'-ATCCCTCTACATCTTTGTCAT-3'    (SEQ ID NO: 1)
and

Antisense:
5'-ATGACAAAGATGTAGAGGGAT-3'    (SEQ ID NO: 2)
Or

Sense:
5'-CAAGAGGAACAGCACAGCCAA-3'    (SEQ ID NO: 3)
and

Antisense:
5'-TTGGCTGTGCTGTTCCTCTTG-3'    (SEQ ID NO: 4)
```

The DNA templates of the siRNA molecules were cloned into the microRNAs-based short-hairpin RNA interference vector system according to the manufacturer's instruction (Invitrogen, Carlsbad, CA, USA) and transduced into HUVEC cells to express the siRNA molecules. Real-time RT-PCR of GPR4 showed that these two siRNA molecules efficiently down-regulated GPR4 expression by more than 80% in HUVEC cells (FIG. 4C). A control miRNA without GPR4 sequence homology did not inhibit GPR4 expression (FIG. 4C).

Effects on HUVEC cell adhesion: HUVEC cells with GPR4 siRNA or control siRNA were treated with different pHs, and the U937-HUVEC cell adhesion assay was performed. The acidosis/GPR4-induced HUVEC cell adhesion was diminished by these two GPR4 siRNAs but not the control siRNA (FIG. 4F). These results indicate that the expression of GPR4 is required for acidosis-induced adhesion of HUVEC endothelial cells.

Figure 6:
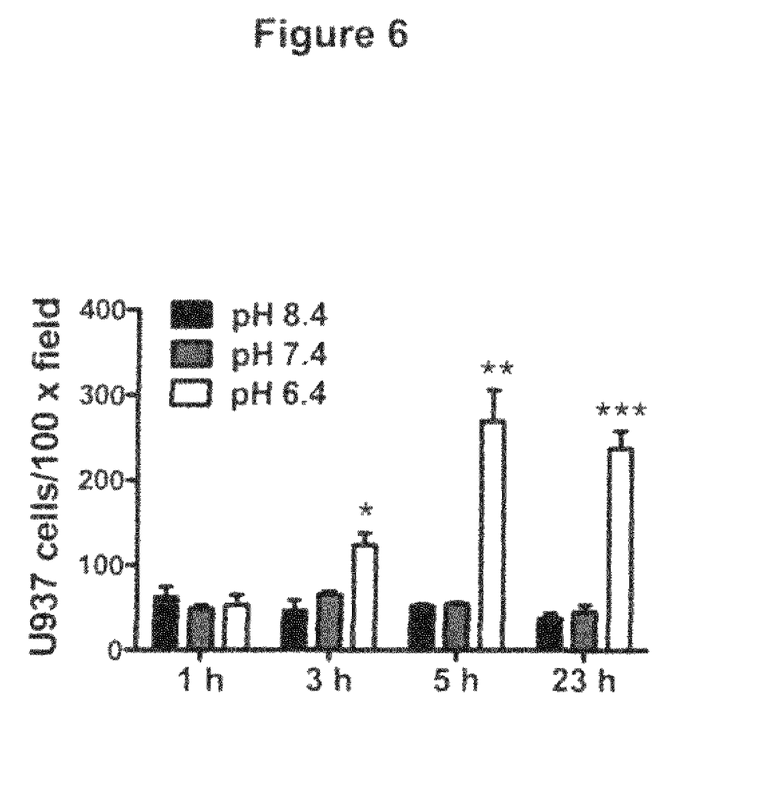
FIG. 6 sets forth data demonstrating the time course of acidosis/GPR4-induced adhesion of HUVEC cells stably overexpressing GPR4. Results are depicted as the mean±SEM. *, P<0.05; , P<0.01; *, P<0.001; compared with the pH 8.4 groups.

Furthermore, the time course of acidosis/GPR4-induced endothelial cell adhesion was examined. HUVEC/GPR4 cells were treated with EGM-2/HEM medium at pH 6.4, pH 7.4 and pH 8.4 for 1, 3, 5, and 23 hours and then U937 monocytes were added for the adhesion assay. As shown in FIG. 6, by 1 hour no increase of HUVEC cell adhesion was detected. By 3 hours, pH 6.4 (400 nM $H^+$), compared to pH 8.4 (4 nM $H^+$) and pH 7.4 (40 nM $H^+$), significantly increased the adhesiveness of HUVEC cells. By 5 to 23 hours, the peak induction of HUVEC cell adhesion by acidic pH was observed. The results show that the acidosis/GPR4-induced HUVEC cell adhesion is a quick process that takes place within 3 hours after the acidic pH stimulation.

Example 4

Figure 7:
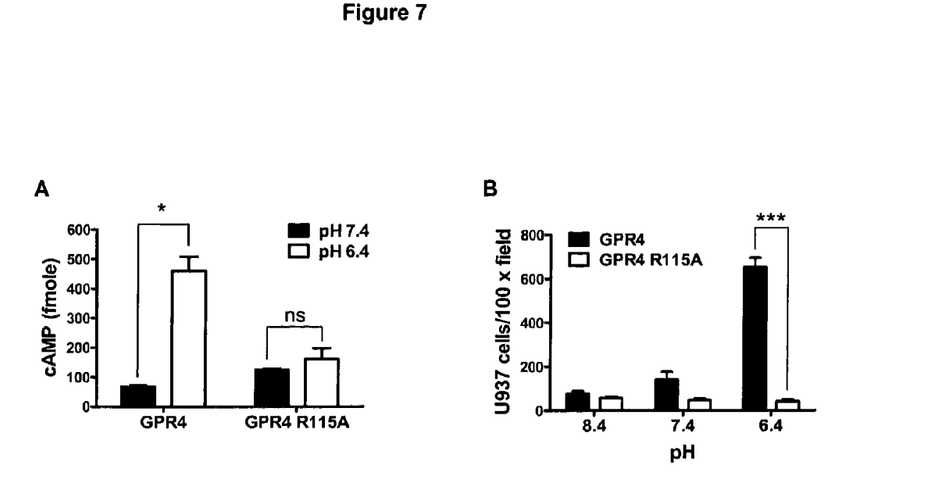
FIG. 7A sets forth data demonstrating the production of cAMP in HUVEC endothelial cells with the overexpression of GPR4 or GPR4 DRY motif mutant (R115A). *, P<0.05; ns, not significant (P>0.05). Error bars are the mean±SEM.
FIG. 7B sets forth data demonstrating that the mutation (R115A) of the GPR4 DRY motif abolishes acidosis/GPR4-induced HUVEC cell adhesion. ***, P<0.001. Error bars are the mean±SEM.

Gs/cAMP Signaling Is Important for Acidosis/GPR4-Induced Endothelial Cell Adhesion GPCRs are cell surface receptors that transduce signals mainly through G protein coupling, but G protein-independent pathways also exist. To delineate downstream signaling pathways involved in acidosis/GPR4-induced HUVEC cell adhesion, a GPR4 mutant was generated with a mutation of the residue arginine 115 to alanine (R115A) of the DRY motif, which is located at the second intracellular loop and is important for G protein signaling. Wildtype GPR4 and the R115A mutant were overexpressed in HUVEC cells at a comparable level as measured by real-time RT-PCR. The activation of wildtype GPR4 by acidosis increased the production of cAMP in HUVEC cells but the GPR4 R115A mutant failed to stimulate cAMP production (FIG. 7A). When treated with acidic pH, HUVEC cells overexpressing the wildtype GPR4 showed an approximately 10 fold increase of adhesion. However, the overexpression of the GPR4 R115A mutant did not stimulate an increase of HUVEC cell adhesion (FIG. 7B). These results indicate that G protein signaling is important for acidosis/GPR4-induced endothelial cell adhesion.

Figure 8:
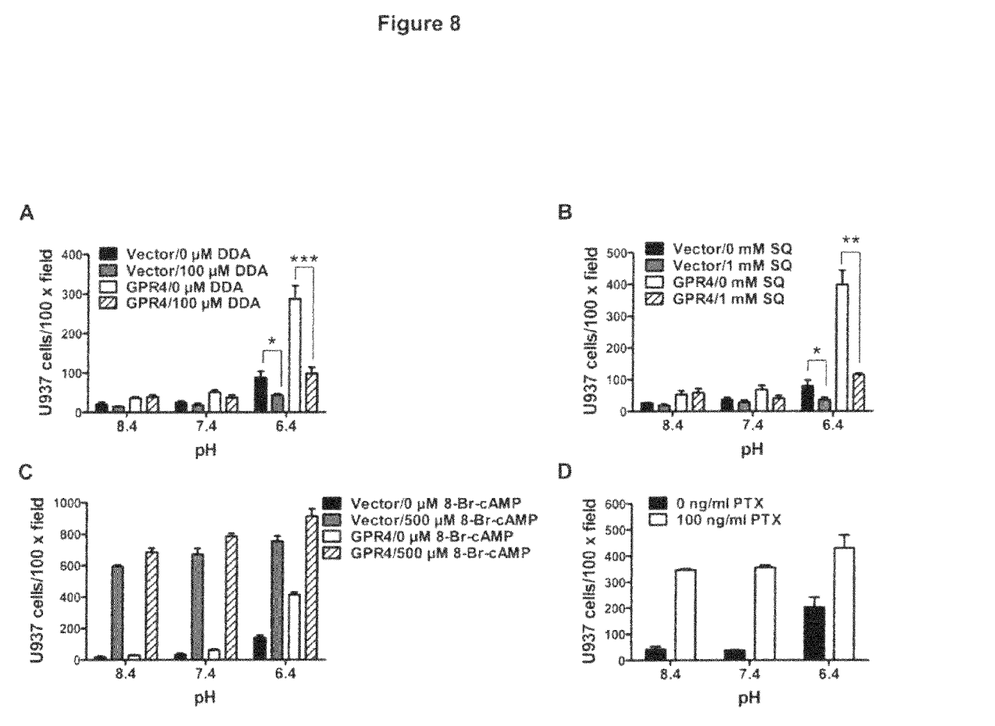
FIG. 8A sets forth data demonstrating that the adenylate cyclase inhibitor, 2',5'-dideoxyadenosine (DDA), diminishes the adhesion of HUVEC cells induced by acidosis/GPR4. *, P<0.05; ***, P<0.001. Error bars are the mean±SEM.
FIG. 8B sets forth data demonstrating that the treatment of the adenylate cyclase inhibitor, SQ 22536, reduces the adhesion of HUVEC cells induced by acidosis/GPR4. *, P<0.05; **, P<0.01. Error bars are the mean±SEM.
FIG. 8C sets forth data demonstrating that the treatment of the cAMP analog, 8-bromo-cAMP, increases the adhesion of HUVEC cells.
FIG. 8D sets forth data demonstrating that the treatment of the Gi inhibitor, pertussis toxin (PTX), increases the adhesion of HUVEC cells.

To further identify downstream pathways, the involvement of the Gs/cAMP pathway was assessed. When HUVEC cells were treated with the adenylate cyclase inhibitor, 2',5'-dideoxyadenosine (DDA), acidosis/GPR4-induced HUVEC adhesion was reduced (FIG. 8A). A similar extent of decrease in HUVEC cell adhesiveness was observed when cells were treated with another adenylate cyclase inhibitor SQ 22536 (FIG. 8B). Consistently, treatment with a cAMP analog, 8-bromo-cAMP, increased the adhesion of HUVEC cells at all tested pHs, mimicking the effects of GPR4 activation (FIG. 8C). In line with this result, treatment of HUVEC/GPR4 cells with pertussis toxin (PTX), which blocks the cAMP inhibitory G protein Gi and increases cAMP level, enhanced HUVEC cell adhesiveness (FIG. 8D). These results show that the Gs/cAMP pathway is important for acidosis/GPR4-induced HUVEC cell adhesion.

Example 5

Figure 9:
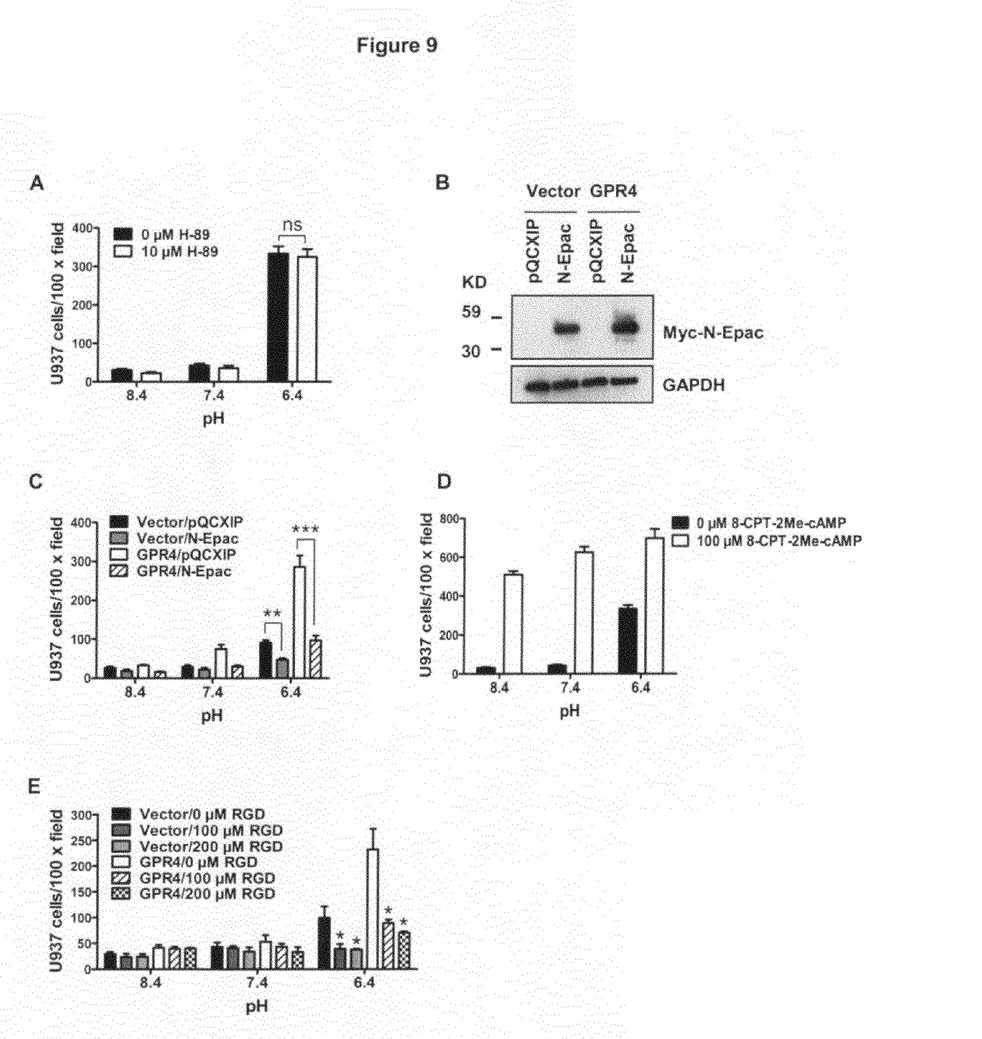
FIG. 9A sets forth data demonstrating that the treatment with the PKA inhibitor H-89 does not affect HUVEC cell adhesion induced by acidosis/GPR4. ns, not significant (P>0.05).
FIG. 9B sets forth data demonstrating the expression of myc-N-Epac detected by Western blot analysis with anti-myc antibodies. GAPDH is used as a loading control.
FIG. 9C sets forth data demonstrating that the inhibition of Epac by the dominant-negative construct myc-N-Epac diminishes acidosis/GPR4-induced HUVEC cell adhesion. , P<0.01; *, P<0.001.
FIG. 9D sets forth data demonstrating that the treatment with the Epac activator 8-CPT-2Me-cAMP increases HUVEC cell adhesion.
FIG. 9E sets forth data demonstrating that the treatment with RGD peptides, the integrin inhibitors, diminishes acidosis/GPR4-induced HUVEC adhesion. *, P<0.05; compared with the vehicle groups. Error bars are the mean±SEM.

The cAMP Effector, Epac, is Involved in Acidosis/GPR4-Induced Endothelial Cell Adhesion Increase of intracellular cAMP can activate several downstream effectors such as PKA (protein kinase A) and Epac (exchange protein directly activated by cAMP). The role of PKA was assessed by treating HUVEC cells with the PKA inhibitor H-89. The results showed that the inhibition of PKA by H-89 did not affect acidosis/GPR4-induced HUVEC cell adhesion (FIG. 9A). To investigate the role of Epac in acidosis/GPR4-induced HUVEC cell adhesion, a dominant-negative Epac mutant, N-Epac, was expressed in HUVEC/vector and HUVEC/GPR4 cells. The pQCXIP empty vector was used as a control. The expression of the myc-tagged N-Epac in HUVEC cells was confirmed by Western blotting (FIG. 9B). The N-Epac dominant-negative mutant lacks the kinase domain and blocks the activity of Epac by competitively binding with the substrates (Hochbaum D. et al. 2008, *J. Biol. Chem.*, Vol. 283, pp. 4464-4468). The results demonstrated that the expression of the N-Epac dominant-negative mutant inhibited acidosis/GPR4-induced HUVEC cell adhesion (FIG. 9C). Consistently, when HUVEC cells were treated with the Epac specific activator 8-CPT-2Me-cAMP, cell adhesion was increased (FIG. 9D). These results suggest that Epac is the downstream cAMP effector that mediates acidosis/GPR4-induced HUVEC cell adhesion. Integrins are downstream targets of Epac and could be potentially involved in acidosis/GPR4-induced HUVEC adhesion. To investigate this possibility, HUVEC cells were treated with RGD peptides that competitively block the RGD binding motif of integrins. Compared to the control, the treatment with RGD peptides inhibited acidosis/GPR4-induced HUVEC cell adhesion (FIG. 9E). These results show that Epac and its downstream effector integrins are important for acidosis/GPR4-induced HUVEC cell adhesion.

What is claimed is:

1. A method of inhibiting vascular endothelial cell adhesion and leukocyte attachment in acidosis conditions, wherein the inhibition of vascular cell adhesion and leukocyte attachment is achieved by inhibiting the proton-sensing receptor GPR4, in particular, with small interfering RNA molecules that have the nucleotide sequences of: sense: 5'-AUCCCUCUACAUCUUUGUCAU-3' (SEQ ID NO:1) and antisense: 5'-AUGACAAAGAUGUAGAGGGAU-3' (SEQ ID NO:2) or sense: 5'-CAAGAGGAACAGCACAGC-CAA-3' (SEQ ID NO:3) and antisense: 5'-UUGGCU-GUGCUGUUCCUCUUG-3' (SEQ ID NO:4).

* * * * *